US007684543B2

(12) United States Patent
Matsuo et al.

(10) Patent No.: US 7,684,543 B2
(45) Date of Patent: Mar. 23, 2010

(54) X-RAY BEAM CONDITIONING DEVICE AND X-RAY ANALYSIS APPARATUS

(75) Inventors: Ryuji Matsuo, Kunitachi (JP); Tetsuya Ozawa, Hino (JP); Katsuhiko Inaba, Ome (JP); Makoto Aoyagi, Akishima (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 0 days.

(21) Appl. No.: 11/476,888

(22) Filed: Jun. 29, 2006

(65) Prior Publication Data
US 2007/0003013 A1  Jan. 4, 2007

(30) Foreign Application Priority Data
Jun. 30, 2005  (JP)  ............... 2005-191611

(51) Int. Cl.
*G21K 1/06* (2006.01)
(52) U.S. Cl. .................. 378/85; 378/145
(58) Field of Classification Search ............ 378/70, 378/71, 82, 84, 85, 156, 145, 72
See application file for complete search history.

(56) References Cited

U.S. PATENT DOCUMENTS

| | | | | |
|---|---|---|---|---|
| 3,160,749 A | * | 12/1964 | Spielberg | 378/85 |
| 3,706,888 A | * | 12/1972 | Wunsch | 378/56 |
| 4,567,605 A | * | 1/1986 | Bartels | 378/85 |
| 5,107,529 A | * | 4/1992 | Boone | 378/157 |
| 5,850,425 A | | 12/1998 | Wilkins | |
| 6,697,454 B1 | * | 2/2004 | Nicolich et al. | 378/85 |
| 2001/0053198 A1 | | 12/2001 | Kikuchi | |
| 2004/0190681 A1 | * | 9/2004 | Omote | 378/71 |

FOREIGN PATENT DOCUMENTS

| | | | |
|---|---|---|---|
| JP | 06130195 A | * | 5/1994 |
| JP | 08-054497 | | 2/1996 |
| JP | 9-49811 | | 2/1997 |
| JP | 2002-139598 | | 5/2002 |
| WO | WO 96/37898 | | 11/1996 |

OTHER PUBLICATIONS

Ise et al., "X-Ray scattering study of ionic colloidal crystals," *Current Opinion in Colloid & Interface Science*, 2001, vol. 6, pp. 126-131, Elsevier Science, Ltd.
European Search Report in corresponding European Application No. 06253351 dated Jul. 16, 2009.

* cited by examiner

*Primary Examiner*—Edward J Glick
*Assistant Examiner*—Mona M Sanei
(74) *Attorney, Agent, or Firm*—Buchanan Ingersoll & Rooney PC

(57) ABSTRACT

An X-ray beam conditioning device that has a crystal holder and a motor is provided. The crystal holder supports a first crystal block and a second crystal block, each of which diffracts X-ray by a specific diffraction angle. The motor can rotate the crystal holder around an axis extending at right angles to a plane including an optical axis of X-ray and can fixedly support the crystal holder at the rotated position. The crystal holder holds the first and second crystal blocks at such angles to each other such that both crystal blocks diffract X-ray. The optical axes of the two crystal blocks can be adjusted by rotating the crystal holder about the axis, that is, the only one axis.

20 Claims, 12 Drawing Sheets

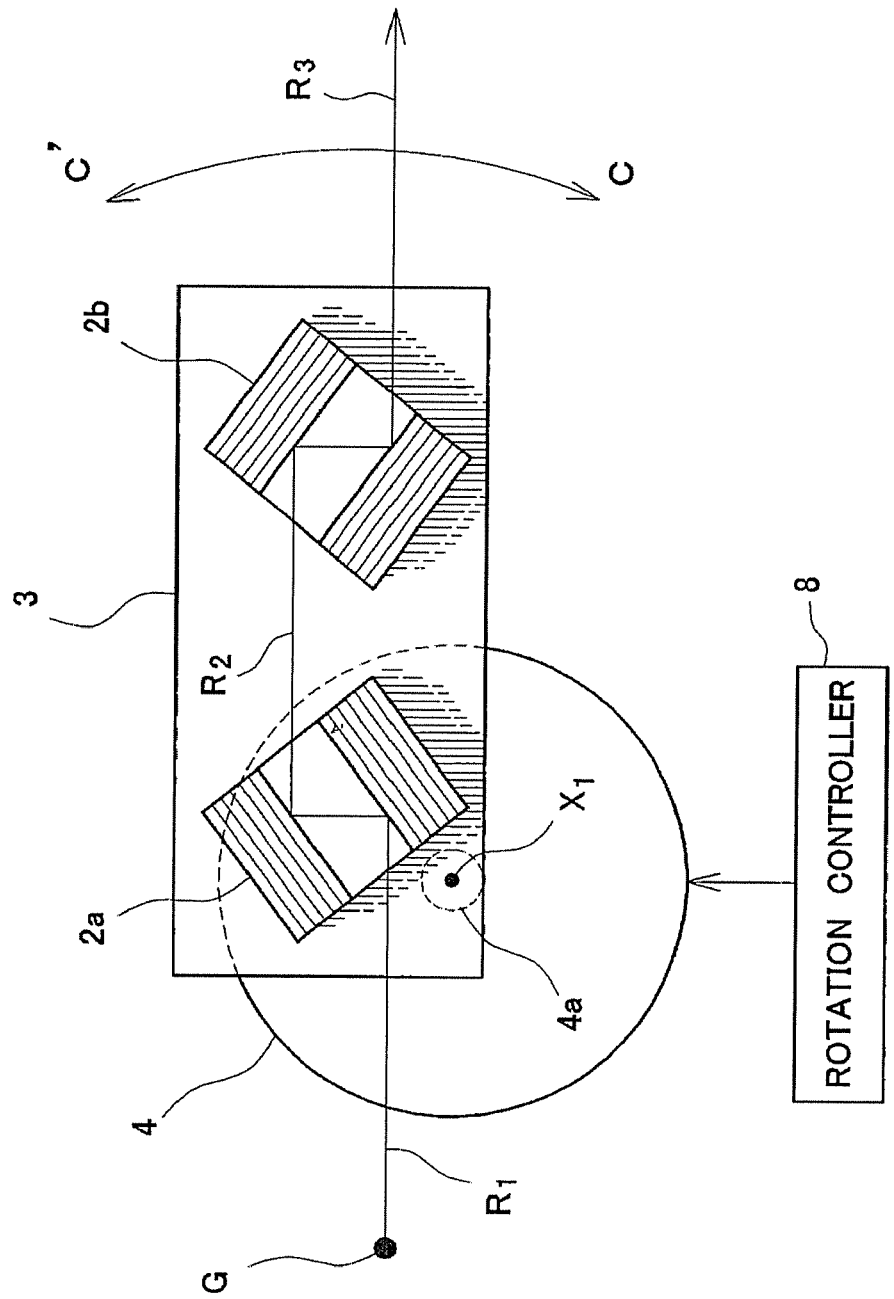

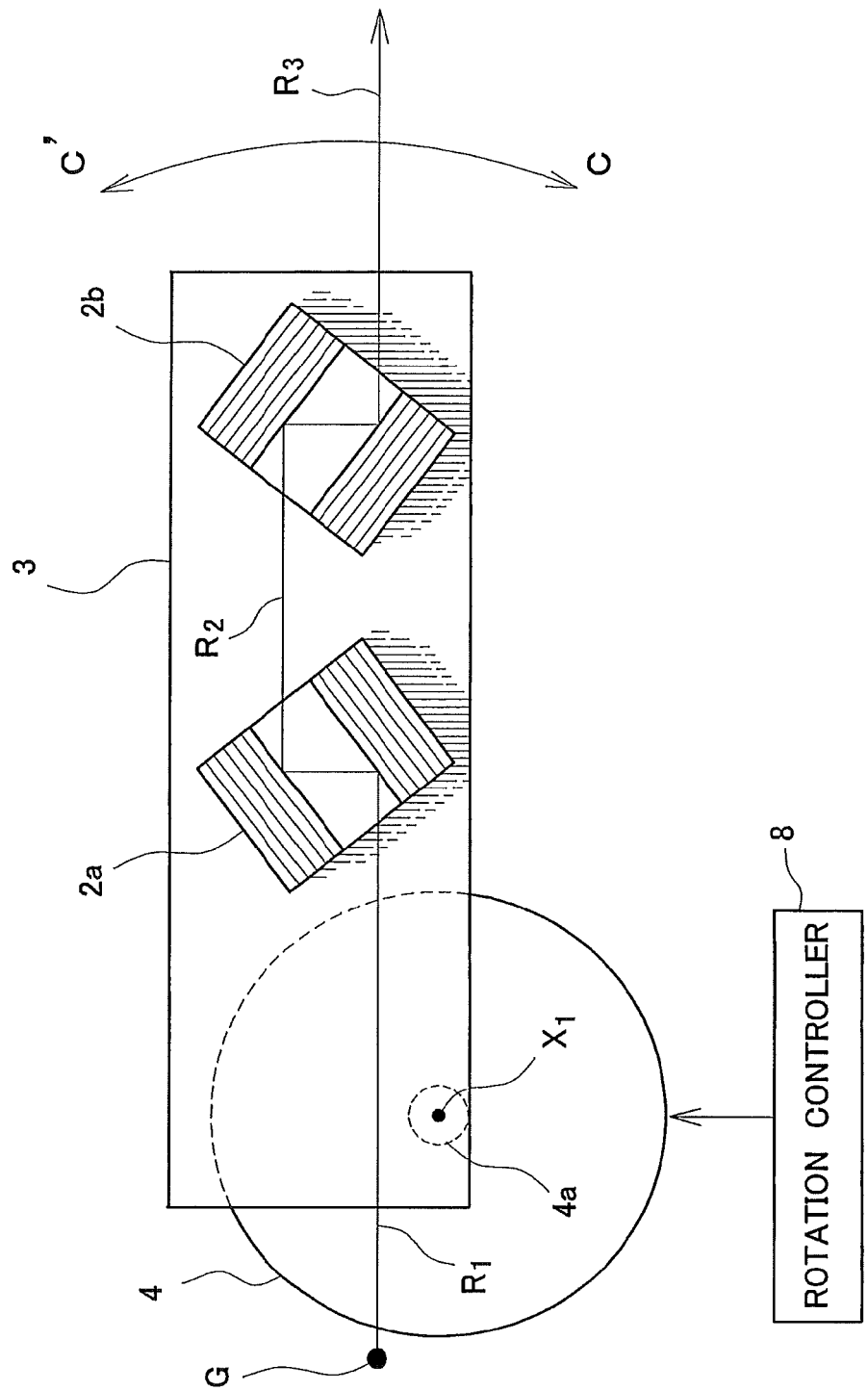

X-RAY BEAM CONDITIONING DEVICE AND X-RAY ANALYSIS APPARATUS

BACKGROUND OF THE INVENTION

1. Field of the Invention

The present invention relates to an X-ray beam conditioning device such as a monochromator or an analyzer, and an X-ray analysis apparatus which uses an X-ray beam conditioning device.

2. Description of the Related Art

Hitherto, an X-ray beam conditioning device such as a monochromator or an analyzer has been used in X-ray analysis apparatus such as X-ray diffractometer. The monochromator is an X-ray beam conditioning device that is used mainly to perform monochromatization, converting X-rays containing X-rays of different wavelengths to monochromatic X-ray. In most X-ray analysis apparatus, the monochromator is arranged between an X-ray source and a sample (namely, at the upstream side of the sample, with respect to the traveling direction of X-ray).

The analyzer is another type of an X-ray beam conditioning device and used mainly to enhance the angular resolution of X-ray in X-ray analysis apparatuses. In the X-ray analysis apparatus, the analyzer is arranged between the sample and an X-ray detecting means (namely, at the downstream side of the sample, with respect to the traveling direction of X-ray). The analyzer receives, for example, X-ray (e.g., diffracted X-ray, scattered X-ray, reflected X-ray and spectroscopic X-ray) emanating from the sample, and selects X-ray that satisfies predetermined condition of wavelength to emit it to the X-ray detecting means, to thereby enhance the angular resolution of X-ray.

A monochromator of the type shown in FIG. 1A is known in the art. As FIG. 1A shows, two channel-cut crystals 101*a* and 101*b* are arranged in an X-ray path $X_0$. Each of the channel-cut crystals 101*a* and 101*b* is provided with an angle-controlling mechanism, respectively. To adjust the optical axis, the channel-cut crystal 101*b* at downstream side is removed and the channel-cut crystal 111*a* at upstream side is rotated in the direction of arrow A1 and set into alignment with the X-ray path $X_0$. Then, the channel-cut crystal 101*b* at downstream side is attached and rotated in the direction of arrow A2, thereby achieving the angle adjustment of the channel-cut crystals 101*a* and 101*b*.

A monochromator of another type shown in FIG. 1B is known in the art. As FIG. 1B shows, this monochromator has mechanisms 102*a* and 102*b* for moving the channel-cut crystals 101*a* and 101*b*, respectively, away from the X-ray path $X_0$. To adjust the optical axis, one of the channel-cut crystals is moved away from the X-ray path $X_0$ as indicated by arrow B1 or B2, and the other channel-cut crystal on the X-ray path $X_0$ is set into alignment with the X-ray path $X_0$.

Still another type of a monochromator shown in FIG. 2 is known in the art. As shown in FIG. 2, axes Xa and Xb for adjusting the angles of the channel-cut crystals 101*a* and 101*b* are located apart from the X-ray path $X_0$. When the optical axis of X-ray is being adjusted, each of channel-cut crystals 101*a* and 101*b* is greatly rotated around the corresponding axis Xa or Xb, thereby moving the channel-cut crystals 101*a* and 101*b* outside of the X-ray path $X_0$. A monochromator of this type is disclosed in, for example, FIG. 1 of Jpn. Pat. Appln. Laid-Open Publication No. 9-049811. In this monochromator, the angle adjustment of channel-cut crystals and the mechanism for retreating the crystals from the X-ray path are both accomplished by rotating the crystals around a common axis.

SUMMARY OF THE INVENTION

The conventional monochromator shown in FIG. 1A has no mechanisms for retreating the crystals 101*a* and 101*b* from the X-ray path $X_0$. Therefore, an operator must manually remove and attach the channel-cut crystals 101*a* and 101*b* in order to adjust the optical axis. In other words, the optical axis cannot be automatically adjusted.

The conventional monochromator illustrated in FIG. 1B has indeed mechanisms for retreating the crystals 101*a* and 101*b* from the X-ray path $X_0$. However, a crystal-rotating mechanism and a crystal-sliding mechanism must be provided for each channel-cut crystal. These mechanisms are complex in structure. Further, the mechanisms that control them are necessarily complex, too. Consequently, it is very difficult to achieve automatic adjustment of the optical axis. In addition, any apparatus incorporating this monochromator, such as an X-ray analysis apparatus, cannot be formed compact because it should have an inner space in which the channel-cut crystals can move away from the X-ray path $X_0$.

Any channel-cut crystals of four-times reflection type must undergo angle adjustment of very high precision. When one channel-cut crystal is set on the X-ray path $X_0$ after it is moved away from the path $X_0$, both channel-cut crystals must be adjusted again in terms of angle. Thus, it is very troublesome to adjust the optical axis.

In the monochromator shown in FIG. 2 of Jpn. Pat. Appln. Laid-Open Publication No. 9-049811, the channel-cut crystals 101*a* and 101*b* are rotated around the axes Xa and Xb through extremely large angles in order to be retreated from the X-ray path $X_0$. Therefore, the angle reproducibility of the channel-cut crystals 101*a* and 101*b* becomes low. Assume that one of the channel-cut crystals 101*a* and 101*b* is rotated by an angle as large as 180° and moved away from the X-ray path $X_0$, and then is rotated back to an angle position on the X-ray path $X_0$. In this case, this channel-cut crystal may fail to assume an angle position that is identical to the initial one on the X-ray path $X_0$ due to an influence of the gear backrush included on a rotation drive mechanism or any other factor. This phenomenon seems to be more prominent as the angle by which the crystal is rotated away from the X-ray path $X_0$ increases.

Like the conventional monochromator of FIG. 1B, the monochromator of FIG. 2 must have an inner space in which the channel-cut crystals can move away from the X-ray path $X_0$. Any apparatus incorporating this monochromator, such as an X-ray analysis apparatus, cannot be formed compact.

The present invention has been made in view of the above-mentioned problems with the conventional X-ray beam conditioning devices. An object of this invention is to provide an X-ray beam conditioning device that is compact and has an optical axis which can be easily adjusted or automatically adjusted. Another object of the invention is to provide an X-ray analysis apparatus that incorporates the X-ray beam conditioning device.

(configuration of the X-Ray Beam Conditioning Device)

An X-ray beam conditioning device according to the present invention comprises: a crystal-supporting means for supporting a first crystal block and a second crystal block, each of which diffracts X-ray by a specific angle; and a crystal-angle adjusting means for rotating the crystal-supporting means around an axis extending at right angles to a plane including an optical axis of the X-ray, and fixedly supporting the crystal-supporting means at thus rotated position; wherein the crystal-supporting means holds the first and second crystal blocks at such angles to each other that both crystal blocks diffract X-ray.

In the X-ray beam conditioning device, the crystal-supporting means holds the first and second crystal blocks, precisely maintaining the crystal blocks at a prescribed angle to each other. Hence, when only one crystal block, for example the first crystal block, is adjusted in terms of angle, the second crystal block is automatically set at a correct angle position. Thus, the second crystal block need not be moved away from the X-ray path or adjusted in terms of angle. It is very easy to adjust the optical axis. The optical axis can therefore be automatically adjusted. Neither the first crystal block nor the second crystal block needs to be moved away from the X-ray path, no space for motion of the crystal blocks is required. Therefore, the X-ray beam conditioning device can be formed compact, and any X-ray analysis apparatus that incorporates the device can be formed compact, too.

In the X-ray beam conditioning device according to the present invention, the first crystal block and the second crystal block are preferably channel-cut crystals. A channel-cut crystal is one formed by cutting a groove (or channel) in a crystal block of germanium, silicon or the like. The opposing sides of the groove can reflect X-ray. If the crystal blocks are channel-cut crystals, the device can completely monochromatise an incident beam and can acquire a high angular resolution.

In the X-ray beam conditioning device according to the present invention, the first crystal block may be positioned nearer an X-ray source than the second crystal block. Then, the crystal-angle adjusting means preferably rotates the crystal-supporting means to change an angle at which X-ray generated by the X-ray source is applied to one X-ray reflecting surface of the first crystal block.

With such a construction, the crystal-angle adjusting means can serve to change the angle at which X-ray is applied to the first crystal block. Moreover, once the first crystal block is set at such a position that it can reflect (or diffract) X-ray, the second crystal block can automatically reflect (or diffract) X-ray, without being adjusted at all.

In the X-ray beam conditioning device according to the present invention, the rotation axis of the crystal-supporting means preferably extends in one X-ray reflecting surface of the first crystal block as shown in FIG. 3, if the first crystal block is positioned nearer an X-ray source than the second crystal block. Alternatively, the rotation axis of the crystal-supporting means may extend in through the first crystal block as is illustrated in FIG. 5A. Still alternatively, the rotation axis of the crystal-supporting means may extend outside the first crystal block and pass a point closer to the X-ray source than to the first crystal block, as is illustrated in FIG. 5C.

In the X-ray beam conditioning device according to the present invention, the crystal-angle adjusting means preferably has a motor whose output shaft can be controlled in terms of rotation angle. In this case, the crystal-supporting means should be coupled directly to the output shaft of the motor. Alternatively, the crystal-angle adjusting means may have a rotary mechanism having a tangent bar. If this is the case, the crystal-supporting means is preferably be secured to an output shaft of the rotary mechanism of tangent bar type.

(Configuration of the X-Ray Analysis Apparatus)

An X-ray analysis apparatus according to the present invention comprises: an X-ray source that generates X-ray to be applied to a sample; an X-ray detecting means for detecting X-ray emitted from the sample; and an X-ray beam conditioning device that is arranged between the X-ray source and the sample. The X-ray beam conditioning device may be constituted by any one of the X-ray beam conditioning devices described above. In the apparatus, the X-ray beam conditioning device is located upstream of the sample. That is, it is of the type in which the X-ray beam conditioning device functions as a monochromator.

The X-ray beam conditioning device according to the present invention can fully monochromatize incident X-ray and can acquire a high angular resolution. Therefore, it can fully perform its function when it is used in an X-ray analysis apparatus that needs to accomplish high-precision measuring. X-ray analysis apparatuses required to accomplish high-precision measuring may be a rocking-curve measuring apparatus, a reciprocal space map measuring apparatus, a reflectivity measuring apparatus, and the like.

The rocking-curve measuring apparatus is an apparatus in which X-ray emanating from a sample is detected by an X-ray detector fixed at a predetermined angular position(2θ) relative to incident X-ray, while changing the incident angle (ω) of X-ray applied to the sample over a very narrow range. Result provided by the apparatus is a rocking curve defined in a coordinate graph by plotting the angle change of sample on the axis of abscissas and plotting the X-ray intensity on the axis of ordinates.

The reciprocal space map measuring apparatus is an apparatus that measures X-ray emanating from a sample by scanning the incident angle(ω) of X-ray applied to the sample while changing the angle(2θ) of an X-ray detector little by little. Result provided by the apparatus is a reciprocal space map in which the incident angles(ω) are plotted on the axis of abscissas and the diffraction angles(2θ) are plotted on the axis of ordinates.

The reflectivity-measuring apparatus is an apparatus that sets an incident angle at which X-ray apply to the sample, to a small angle (for example, 0.1° to 4°), and detects X-ray totally reflected by the sample. Result provided by this apparatus is a reflectivity curve defined in a coordinate graph by plotting the diffraction angle(2θ) on the axis of abscissas and plotting the X-ray intensity I on the axis of ordinates.

An X-ray analysis apparatus according to the present invention comprises an X-ray source that generates X-ray to be applied to a sample, an X-ray detecting means for detecting X-ray emitted from the sample, and an X-ray beam conditioning device that is arranged between the sample and the X-ray detecting means. The X-ray beam conditioning device may be constituted by any one of the X-ray beam conditioning devices described above. In the X-ray analysis apparatus, the X-ray beam conditioning device is located downstream of the sample. In other words, the X-ray analysis apparatus is of the type in which the X-ray beam conditioning device functions as an analyzer.

The X-ray beam conditioning device according to the present invention can fully monochromatize incident X-ray and can acquire a high angular resolution. Therefore, it can fully perform its function when it is used in an X-ray analysis apparatus that needs to accomplish high-precision measuring. X-ray analysis apparatuses required to accomplish high-precision measuring may be a rocking-curve measuring apparatus, a reciprocal space map measuring apparatus, a reflectivity measuring apparatus, and the like.

BRIEF DESCRIPTION OF THE DRAWINGS

FIG. 5B is a plan view showing the essential components of still another embodiment of an X-ray beam conditioning device according to the present invention;

FIG. 5C is a plan view showing the essential components of yet another embodiment of an X-ray beam conditioning device according to the present invention;

DETAILED DESCRIPTION OF THE PREFERRED EMBODIMENTS

Figure 1A:
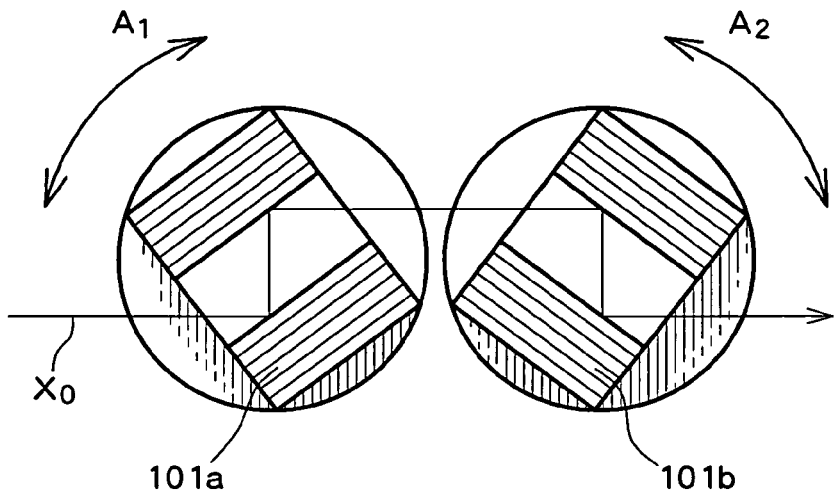
FIG. 1A is a plan view showing an example of a conventional X-ray beam conditioning device.
Figure 1B:
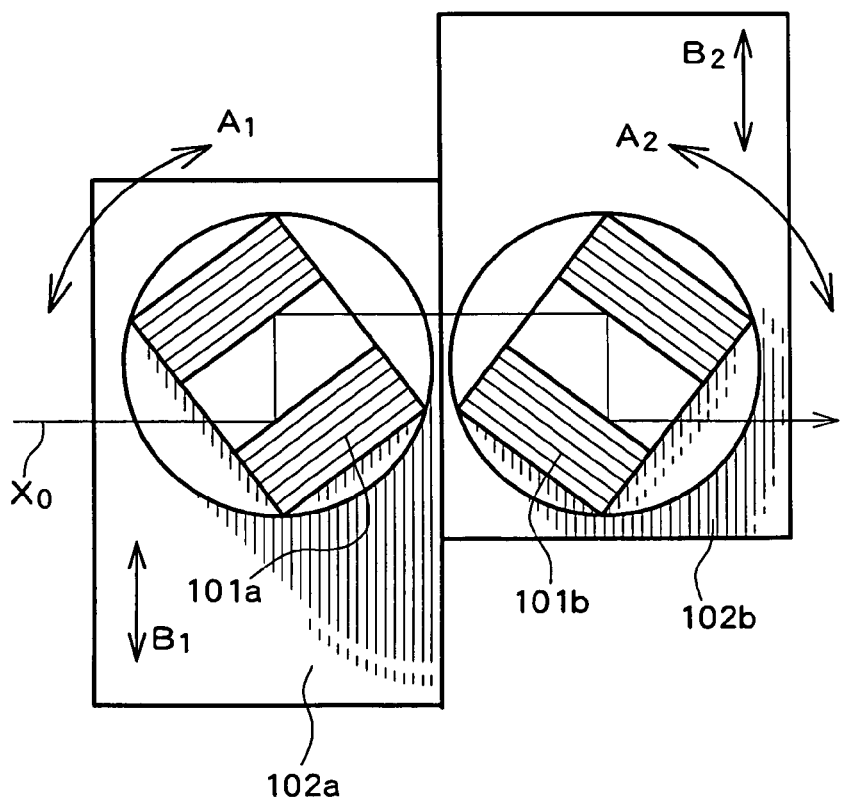
FIG. 1B is a plan view depicting another example a conventional X-ray beam conditioning device.
Figure 2:
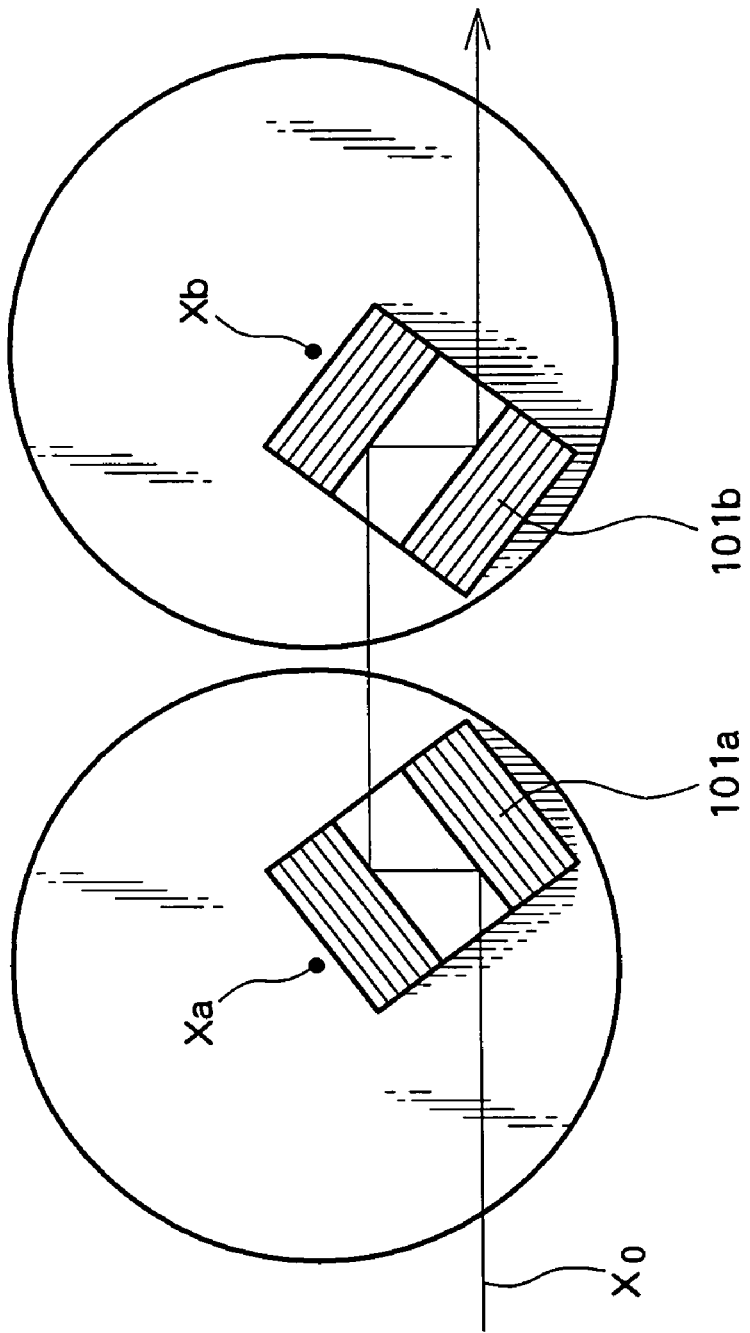
FIG. 2 is a plan view depicting still another example of a conventional X-ray beam conditioning device.

First Embodiment of the X-Ray Beam Conditioning Device

An embodiment of the X-ray beam conditioning device according to the present invention will now be described. Needless to say, the present invention is not limited to the embodiment. The devices will be explained with reference to the accompanying drawings. In the drawings, the components of each device may be illustrated in different scales, thus accentuating the characterizing features of the device.

Figure 3:
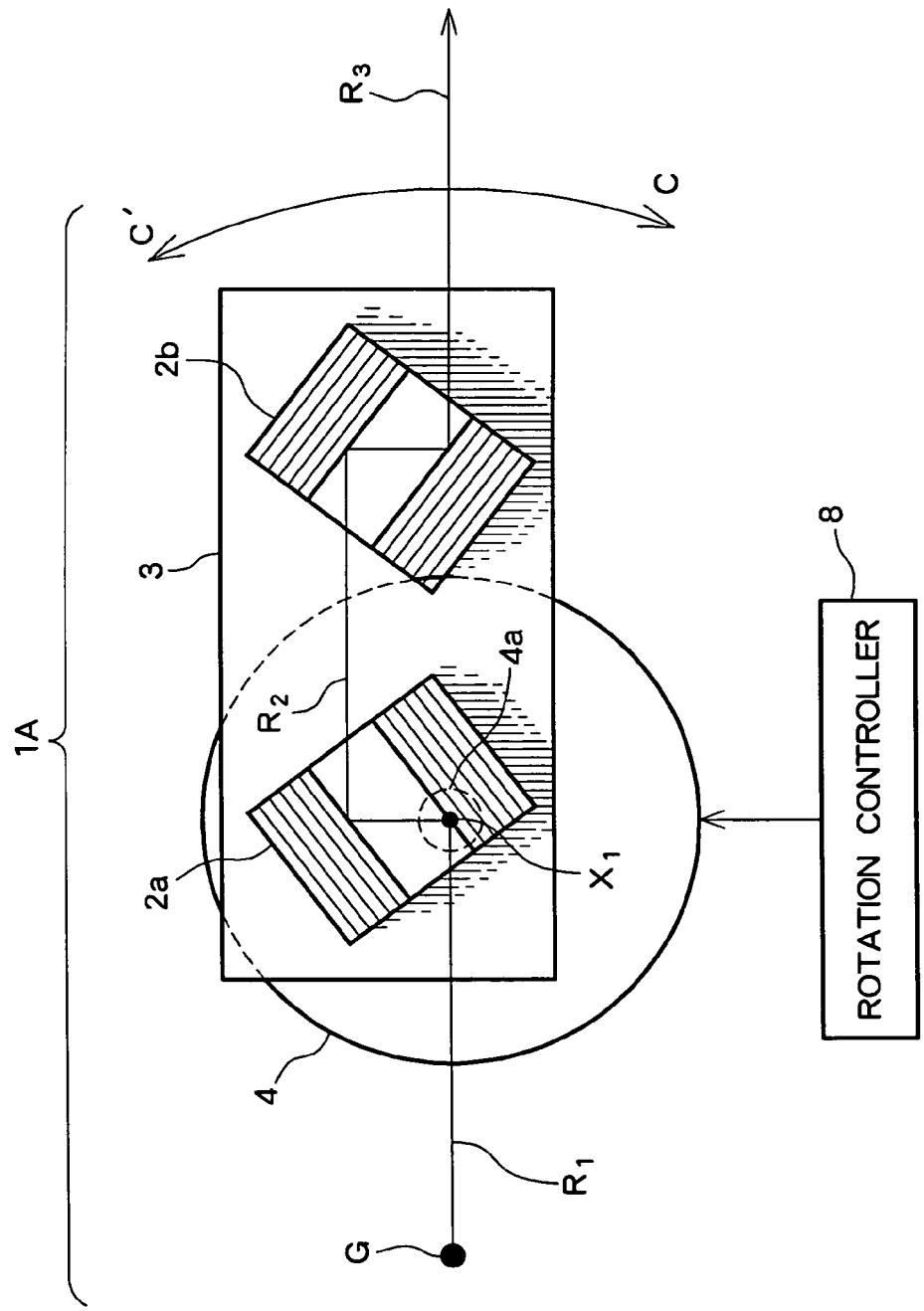
FIG. 3 is a plan view illustrating an embodiment of an X-ray beam conditioning device according to the present invention.

FIG. 3 shows an embodiment of an X-ray beam conditioning device according to the present invention. In FIG. 3, the X-ray beam conditioning device 1A has a first channel-cut crystal 2a used as a first crystal block, a second channel-cut crystal 2b used as a second crystal block, a crystal holder 3 used as crystal-holding means, and a motor 4 used as crystal-angle adjusting means.

Figure 4:
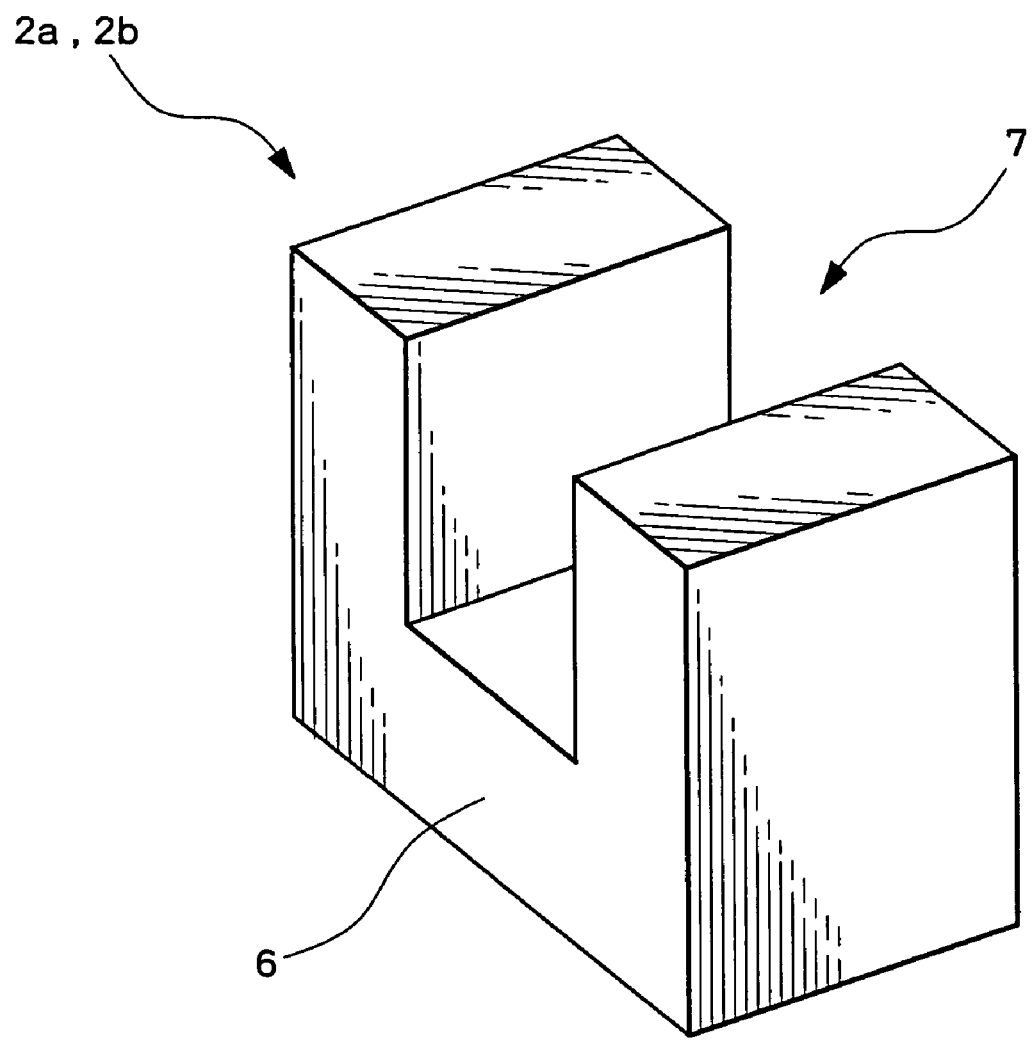
FIG. 4 is a perspective view showing an example of a channel-cut crystal.

As seen from FIG. 4, each of the first channel-cut crystal 2a and the second channel-cut crystal 2b is formed by cutting a groove 7 in a rectangular parallelepiped block 6 made of single crystal. The opposite surfaces of the groove 7 are utilized as reflection surfaces. As FIG. 3 shows, the first channel-cut crystal 2a reflects, at one reflection surface, X-ray R1 emitted from an X-ray generating source G and reflects again thus reflected X-ray at the other reflecting surface, thus emitting X-ray outside. The X-ray generating source G may be an X-ray source composed of a filament and a target, or a sample emitting diffracted X-ray or the like. The second channel-cut crystal 2b reflects X-ray R2 emitted from the first channel-cut crystal 2a, at one reflection surface, and reflects again thus reflected X-ray at the other reflecting surface, thus emitting X-ray outside.

X-ray R3 emitted from the second channel-cut crystal 2b is X-ray that has been obtained by converting the incident X-ray R1 to a monochromatic X-ray (i.e., X-ray of a specific wavelength, selected from the incident X-ray R1). The X-ray satisfies a particular angular resolution (that is, the X-ray is selected from the incident X-ray R1 that proceed in an emanating state and proceed in a specific angle direction). When the X-ray beam conditioning device 1A is used as a monochromator, its function of changing the input X-ray to a monochromatic X-ray is mainly utilized. When the X-ray beam conditioning device 1A is used as an analyzer, its function of enhancing angular resolution is mainly utilized.

The first channel-cut crystal 2a emits reflected X-ray R2 when it is inclined to a specific angle to incident X-ray R1. The second channel-cut crystal 2b emits reflected X-ray R3 when it is inclined to a specific angle to the first channel-cut crystal 2a. The first channel-cut crystal 2a and the second channel-cut crystal 2b are first inclined relatively at specific angles so as to emit X-ray in such a manner and then secured respectively on the crystal holder 3.

The crystals 2a and 2b are secured to the crystal holder 3 with high precision in the place where the X-ray beam conditioning device 1A is manufactured. Once so secured, neither the first channel-cut crystal 2a nor the second channel-cut crystal 2b will be adjusted in position at all in the place where the X-ray beam conditioning device 1A is utilized. In practice, they may be bonded with use of an adhesive, fastened to the crystal holder 3 with screws, or secured to the crystal holder 3 by any other technique. Once the first channel-cut crystal 2a and the second channel-cut crystal 2b are so inclined relatively and secured at the specific relative angle, they always remain in such conditions that each can reflect and emit X-ray of a specific wavelength, wherever the X-ray beam conditioning device 1A is brought and installed.

The crystal holder 3 is coupled to the output shaft 4a of the motor 4, at its back surface opposite to the surface that holds the crystals 2a and 2b. In FIG. 3, the crystal holder 3 is illustrated as nothing more than a rectangle. In fact, however, it is so shaped and structured as to support both crystals 2a and 2b firmly. When the motor 4 is driven and the output shaft 4a therefore rotates, the crystal holder 3 rotates in the direction of arrow C-C' around the axis $X_1$ of the output shaft 4a. The motor 4 is a motor that can be controlled in rotation angle, such as a pulse motor or a servomotor. The motor 4 is driven by a signal output from a rotation controller 8. The rotation controller 8 is connected to a host control unit, as needed. The controller 8 controls the motor 4 in accordance with a rotation-instructing signal transmitted from the host control unit. The host control unit may be a controller incorporated in an X-ray analysis apparatus. It is, for example, such as an X-ray diffractometer.

Figure 5A:
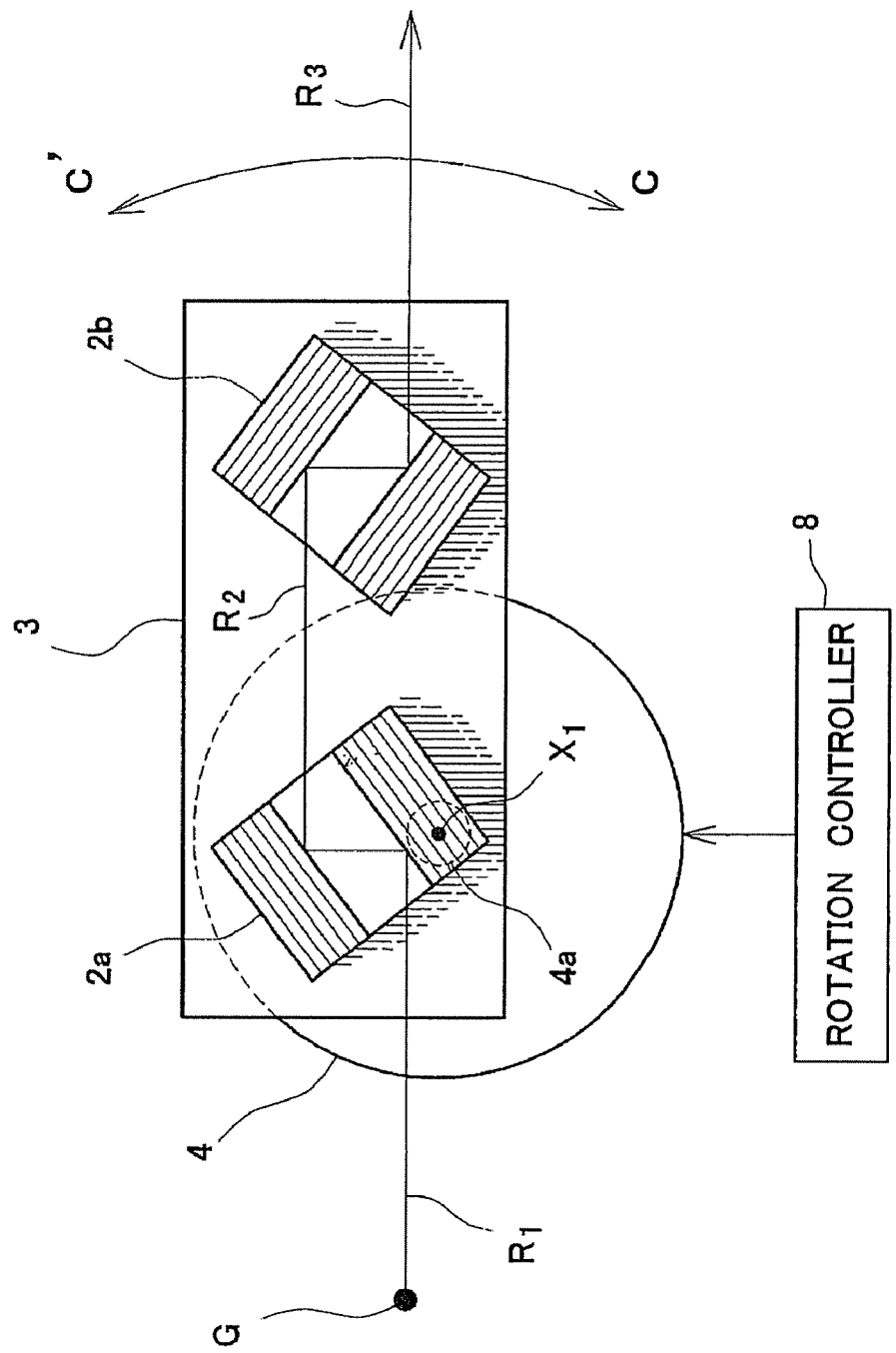
FIG. 5A is a plan view showing the essential components of another embodiment of an X-ray beam conditioning device according to the present invention.

The rotation axis $X_1$ of the crystal holder 3 extends in that reflection surface of the first channel-cut crystal 2a, which first reflects X-ray. Nonetheless, the axis $X_1$ may not be in this reflection surface of the crystal 2a and may pass through the crystal 2a, as is illustrated in FIG. 5A that is a plan view of the X-ray beam conditioning device. Alternatively, the axis $X_1$ may not be in said reflection surface of the crystal 2a and be outside the crystal 2a, as is shown in FIGS. 5B and 5C. In the exemplary embodiments of FIGS. 5B and 5C, the axis $X_1$ extends through the crystal 2a other than at X-ray reflecting surfaces of said first crystal block. In the exemplary embodiment of FIG. 5C, the rotation axis $X_1$ of the crystal holder 3 extends outside the crystal 2a and passes a point closer to the X-ray source G than to the first crystal 2a.

A method in which the X-ray beam conditioning device so configured as described above processes X-rays will be explained below.

(Method of Assembling and Adjusting the Device)

A collimated X-ray has been generated beforehand. The crystal holder 3 of the X-ray beam conditioning device 1A shown in FIG. 3 is positioned on the path of the collimated X-ray. At this point, the second channel-cut crystal 2b that lies behind the first channel-cut crystal 2a is not mounted on the crystal holder 3. Then, the angle of the first channel-cut crystal 2a is adjusted on the crystal holder 3 so that the crystal 2a may reflect X-ray. The crystal 2a, thus adjusted in angle, is secured to the crystal holder 3. Next, the second channel-cut crystal 2b lying behind is provisionally secured to a position on the crystal holder 3 and adjusted in terms of angle so that it may reflect X-ray. The second channel-cut crystal 2b is then secured to the crystal holder 3. Thus, the first channel-cut crystal 2a and the second channel-cut crystal 2b are secured to the crystal holder 3, in a fixed positional relation.

(Method of Performing Minute Adjustment During Use)

An X-ray analysis apparatus to be practically used or an X-ray beam analysis apparatus used as a reference apparatus is adjusted. The reference apparatus is, for example, an apparatus that has a parallel-beam type optical system. The X-ray beam conditioning device 1A shown in FIG. 3 is incorporated into the X-ray analysis apparatus. In this case, the motor 4 shown in FIG. 3 is coupled to the crystal holder 3 and then placed at a prescribed position in the X-ray analysis apparatus. If the motor 4 has already been placed in the X-ray analysis apparatus, the crystal holder 3 is coupled to the output shaft 4a of the motor 4.

The rotation controller 8 gives an instruction, which drives the motor 4. As a result, the crystal holder 3 is scan-rotated in the direction of arrow C-C'. While the scanning rotation of crystal holder 3 takes place, X-ray emitted from the second channel-cut crystal 2b are detected by an X-ray detector. The angular position at which X-ray emitted has the maximum intensity is determined, and the crystal holder 3 is fixed at this position. When X-ray is Cu$K\alpha$1 (having a wavelength of 1.54056 Å) and the crystal is Ge(220), the peak width (i.e., full width of half maximum intensity (FWHM)) of the Cu$K\alpha$1 beam is about 0.005°, and the tail width thereof is therefore about 0.015° To measure this peak, it suffices to provide an angle-measuring range of about 0.1°. Thus, an operation range of about 1° is sufficient, including a tolerance for a peak shift.

The data representing the angular position determined as position at which X-ray has the maximum intensity is stored in a storage medium preliminarily provided in the rotation controller 8 shown in FIG. 3 or in an additional storage medium incrementally provided to the rotation controller 8. The data representing the position of optical systems other than the X-ray beam conditioning device 1A are stored in the storage medium, too.

(Method of Using the Device for Measuring)

In the present embodiment, X-rays having plural wavelengths are diffracted by a crystal four times so that X-ray having a specific wavelength is selected precisely from them. More specifically, in the device of FIG. 3, Cu$K\alpha$1 (having a wavelength of 1.54056 Å) may be used as X-ray, and a Ge (220) crystal may be used as crystal. In this case, the divergence angle of X-ray emitted from the X-ray beam conditioning device 1A can be reduced to about 0.005°. If the X-ray beam conditioning device 1A is employed as a monochromator, the divergence angle of X-ray applied to a sample can be decreased to about 0.005°. If the X-ray beam conditioning device 1A is employed as an analyzer, an X-ray detector can detect X-ray emitted from a sample with angular resolution of about 0.005°. The X-ray beam conditioning device 1A according to this embodiment is fit for use in high-precision measurings, such as measurings for evaluating the single-crystal crystallinity (e.g., rocking-curve measurement and reciprocal-space-map measurement).

(Method of Re-Securing the Device After Minute Adjustment)

Assume that after the minute adjustment described above is completed, the X-ray beam conditioning device 1A according to this embodiment is removed from the X-ray analysis apparatus and then secured back to the X-ray analysis apparatus. Then, the X-ray beam conditioning device 1A and any other optical system may be moved in accordance with the angular position of the device 1A stored in the storage medium, the position of the other optical system and similar factors. This can restore the X-ray optical system to the initial state. The measuring can be started again without the necessity of re-adjusting the X-ray beam conditioning device 1A and the like, unless any other components are removed from the X-ray analysis apparatus.

As can be understood from the foregoing, one angle-adjusting device drives a spectral element of four-times reflection type composed of two channel-cut crystals 2a and 2b in the X-ray beam conditioning device 1A according to the present embodiment. The X-ray beam conditioning device 1A can therefore be made compact. In addition, four crystal surfaces can be minutely adjusted without using special jigs or without performing a complicated operation. The minute adjustment can therefore be automatically achieved by one simple operation, i.e., rotating the crystal holder 3, by using the rotation controller 8 or any other controller, without the necessity of the operator's labor.

Second Embodiment of the X-Ray Beam Conditioning Device

Figure 6:
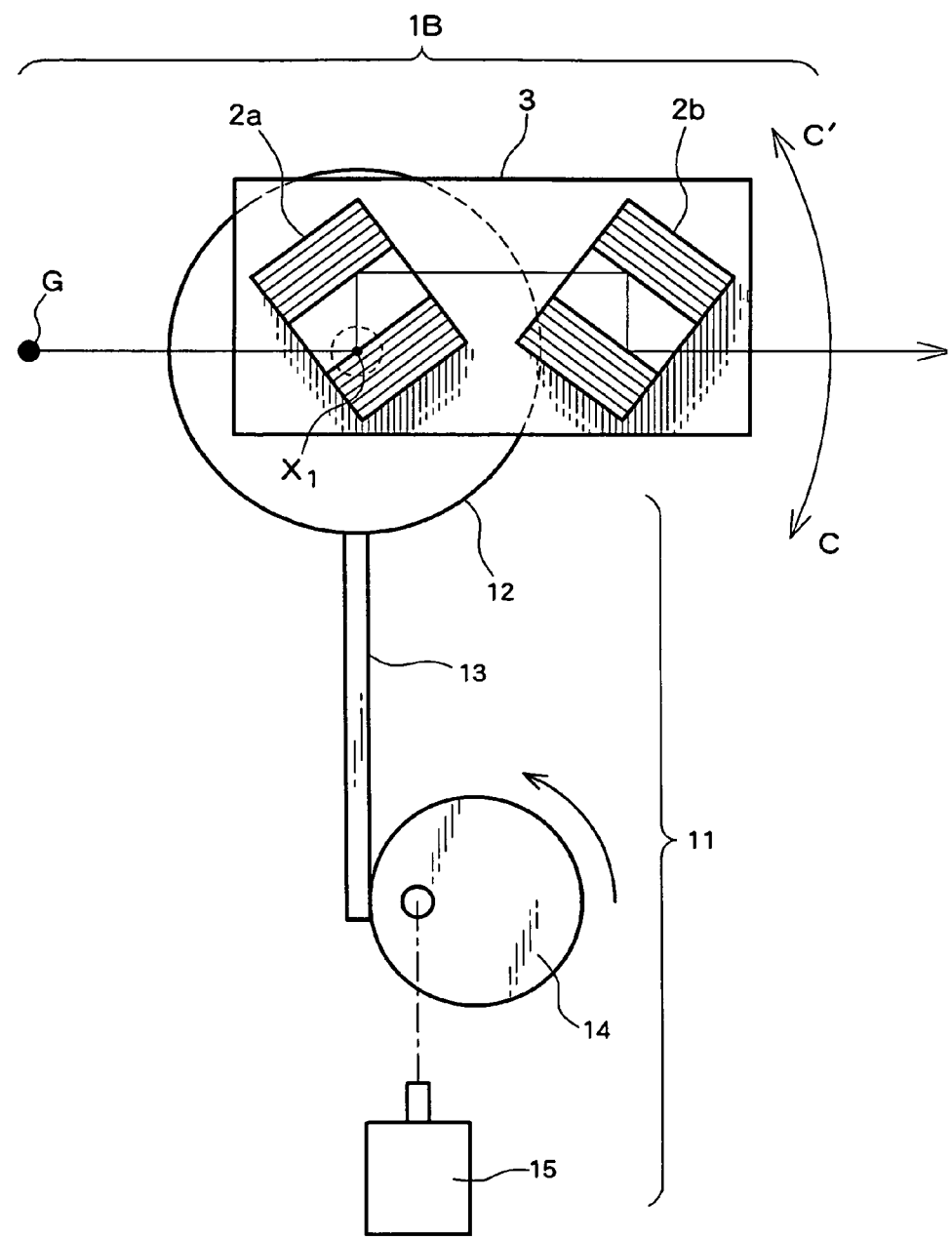
FIG. 6 is a plan view illustrating still another embodiment of an X-ray beam conditioning device according to the present invention.

FIG. 6 is a plan view illustrating another embodiment of an X-ray beam conditioning device according to the present invention. This embodiment differs from the embodiment of FIG. 3 in that the drive device for driving the crystal holder 3 is modified. The component identical to those of FIG. 3 are designated at the same reference numbers in FIG. 6 and will not be described in detail.

In the X-ray beam conditioning device 1B shown in FIG. 6, the crystal holder 3 is supported by a rotary mechanism 11 of tangent bar type. The mechanism 11 has a rotary stage 12 fixedly holding the crystal holder 3, a control rod 13 extending outwards from the rotary stage 12, an eccentric cam 14 abutting on the forward end of the control rod 13, and a motor 15 for rotating the eccentric cam 14. The rotary mechanism 11 of tangent bar type is a minute-rotation mechanism that is known in the art. When the eccentric cam 14 coupled to the motor 15 is rotated, the control rod 13 rotates to control the small rotation angle of the rotary stage 12. The motion range of the crystal holder 3 is about 1° only in this embodiment. Hence, the embodiment can use a rotary mechanism 11 of tangent bar type that has a small effective operation range.

The rotary mechanism 11 of tangent bar type minimizes the small motion that the crystals undergo when the drive system has a backlash or when power is supplied again to the drive motor, to an angle equal to or smaller than the diffraction-limited angle of the crystals. Hence, the X-ray beam conditioning device 1A can operate as if it had four crystals that are completely fixed in place. The crystals may be Ge (440) crystals, and the X-ray applied may be a CuKα1 beam and be separated to the fourth order below the decimal point, i.e., to wavelength of 1.5405 Å. In this case, the minute angle shift of the crystal, which has resulted from the small motion that the crystals undergo when the drive system has a backlash or when power is supplied again to the drive motor, should be reduced to 0.001° or less.

First Embodiment of the X-Ray Analysis Apparatus

Figure 7:
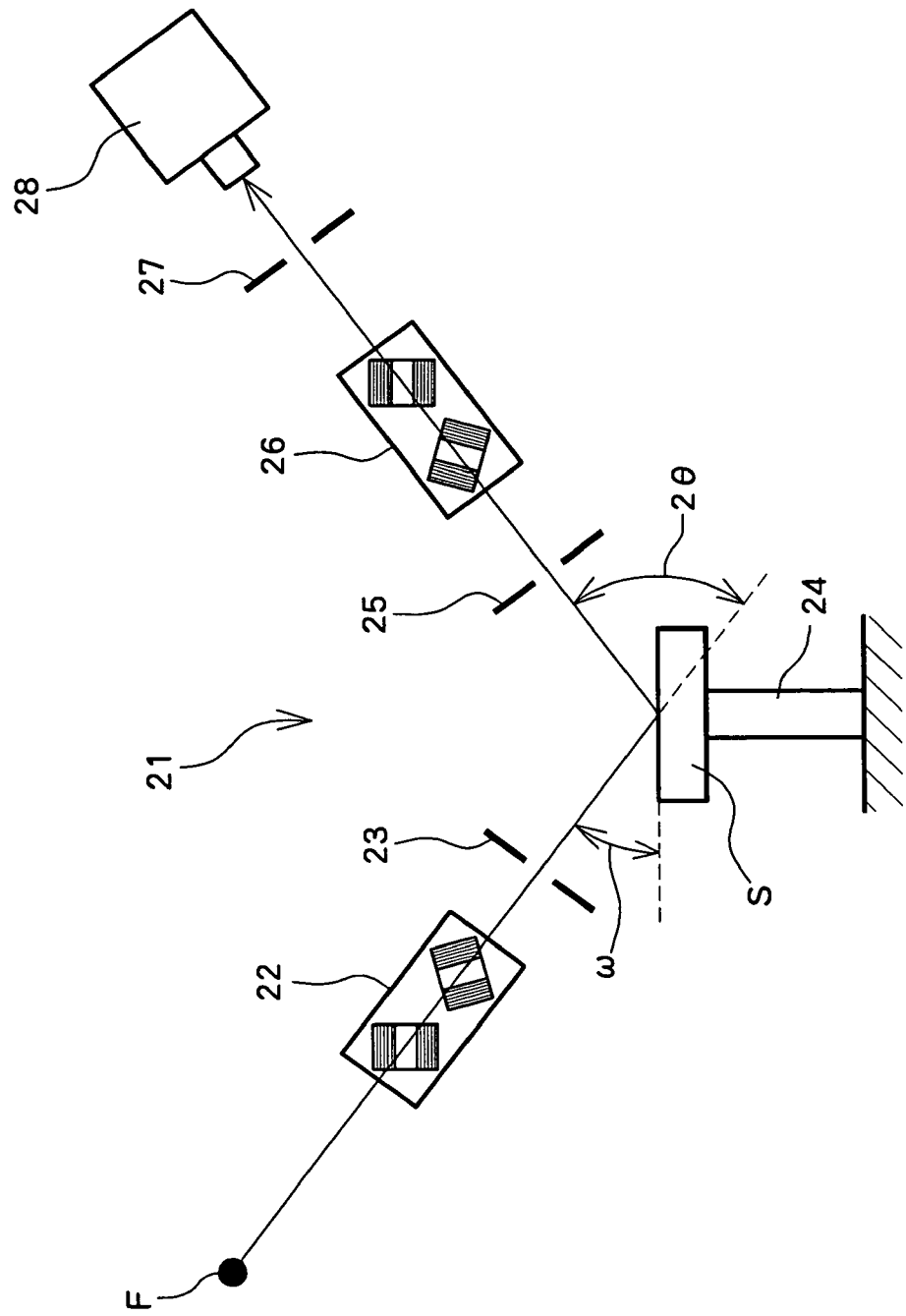
FIG. 7 is a front view depicting an embodiment of an X-ray analysis apparatus according to the present invention.

FIG. 7 shows a first embodiment of an X-ray analysis apparatus according to the present invention. In FIG. 7, the X-ray analysis apparatus 21 has an X-ray source F for generating X-ray, a monochromator 22, a first slit 23, a sample holder 24, a second slit 25, an analyzer 26, a third slit 27, and an X-ray detector 28. The sample holder 24 supports a sample S to be analyzed, and holds the sample S at a prescribed position. The monochromator 22 is constituted by an X-ray beam conditioning device of the same type as the device 1A shown in FIG. 3 or the device 1B shown in FIG. 6. The analyzer 26 is also constituted by an X-ray beam conditioning device of the same type as the device 1A shown in FIG. 3 or the device 1B shown in FIG. 6.

The X-ray source F is of the type in which a filament is heated to emit thermoelectrons, and the thermoelectrons impinge on a target, which emits X-ray. If the target has a surface region made of Cu(copper), it can generate X-ray that contains characteristic X-ray of CuKα. The X-ray detector 28 is constituted by a so-called zero-dimensional counter that is configured to receive X-ray in a point-shaped region. An example of the zero-dimensional counter is scintillation counter (SC).

X-ray emitted from the X-ray source F is applied to the monochromator 22. The monochromator 22 converts the X-ray to a parallel and monochromatic X-ray. X-ray thus rendered monochromatic and parallel, is applied through the first slit 23 to the sample S. If the sample S and X-ray applied to it satisfy prescribed conditions, the sample S generates X-ray (e.g., diffracted X-ray, scattered X-ray, reflected X-ray and spectroscopic X-ray). The X-ray emanating from the sample S is applied through the second slit 25 to the analyzer 26. The analyzer 26 selects X-ray that satisfies a particular angular resolution and emits the X-ray to the downstream side. The X-ray selected is applied through the third slit 27 to the X-ray detector 28. The X-ray detector 28 generates a signal that corresponds to the intensity of the X-ray it has received. From this signal, there will be calculated the intensity of X-ray. In the ordinary X-ray analysis apparatus, the X-ray intensity I is calculated for each rotation angle (2θ) of the X-ray detector 28 relative to the incident X-ray, and is stored as measured data in a form of (2θ, I) in a file provided in the storage medium.

The monochromator 22 and the analyzer 26 are constituted by an X-ray beam conditioning device of the same type as the device 1A shown in FIG. 3 or the device 1B shown in FIG. 6. Both the monochromator 22 and the analyzer 26 may be used, or only one of them may be used. As described above, the spectral element of four-times reflection type composed of two channel-cut crystals 2a and 2b is driven by one angle-adjusting device in the X-ray beam conditioning device 1A or 1B according to the present embodiment. The X-ray beam conditioning device 1A or the like can therefore be made compact. It follows that the x-ray analysis apparatus 21 that incorporates two X-ray beam conditioning devices (including the device 1A) can be made compact, too.

As pointed out above, four crystal surfaces can be minutely adjusted without using special jigs or without performing a complicated operation in the X-ray beam conditioning device 1A or the like. Hence, in the X-ray analysis apparatus 21 having the X-ray beam conditioning device 1A or the like, the monochromator 22 and the analyzer 26 can be adjusted very easily. Since four crystal surfaces can be minutely adjusted by one simple operation, i.e., rotating the crystal holder 3, the minute adjustment can be automatically achieved by using the rotation controller 8 or any other controller, without the necessity of the operator's labor. Thus, in the X-ray analysis apparatus 21 having the X-ray beam conditioning device 1A or the like, too, the minute adjustment can be automatically performed on the monochromator 22 and the analyzer 26.

Second Embodiment of the X-Ray Analysis Apparatus

Figure 8A:
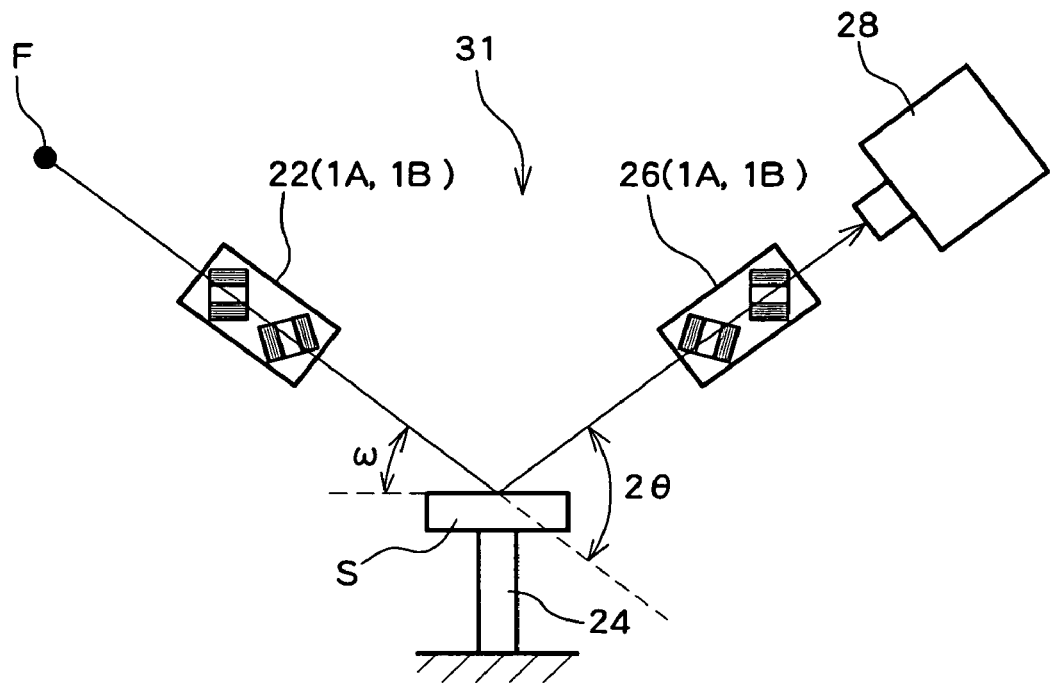
FIG. 8A is a front view showing another embodiment of an X-ray analysis apparatus according to the present invention.

FIG. 8A depicts another embodiment of an X-ray analysis apparatus according to the present invention. In the embodiment the present invention is applied to a rocking-curve measuring apparatus. Note that FIG. 8A only outlines the X-ray analysis apparatus. Accordingly, FIG. 8A shows the essential components only, not illustrating the lesser components of this X-ray analysis apparatus.

The rocking-curve measuring apparatus 31 has an X-ray source F, a monochromator 22, a sample holder 24, an analyzer 26, and an X-ray detector 28. The sample holder 24 supports a sample S to be analyzed, and holds the sample S at a prescribed position. The monochromator 22 and the analyzer 26 are each constituted by an X-ray beam conditioning device of the same type as the device 1A shown in FIG. 3 or the device 1B shown in FIG. 6.

Figure 8B:
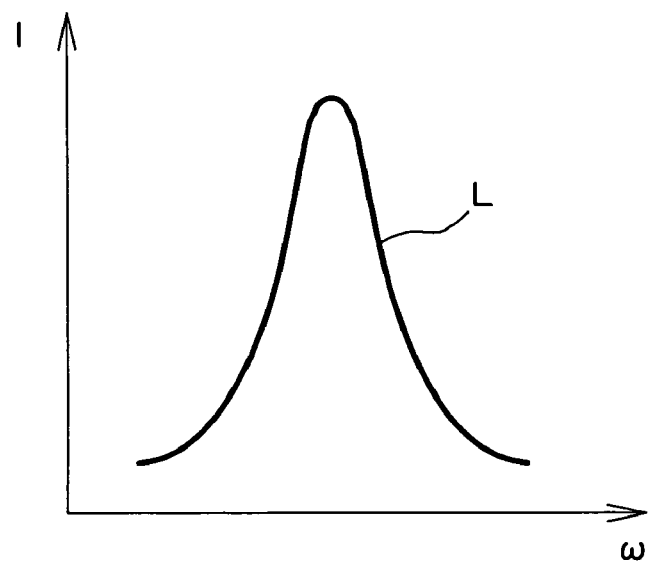
FIG. 8B is a diagram representing the results of measuring performed by using the apparatus shown in FIG. 8A.

In the rocking-curve measuring apparatus 31, the X-ray detector 28 detects X-ray diffracted by the sample S, while it remains at predetermined angle 2θ to the incident X-ray and while the incidence angle ω of X-ray applied to the sample S is changed over a narrow range (namely, small angle range). The measuring results provided by the rocking-curve measuring apparatus 31 are recorded in the form of a rocking curve L shown in FIG. 8B, in which the sample rocking angle ω is plotted on the axis of abscissas and the X-ray intensity I is plotted on the axis of ordinates.

To enable the rocking-curve measuring apparatus 31 to provide reliable data, it is desirable to irradiate the sample S with X-ray that has been completely monochromatised. For the same purpose, it is desired that only X-ray satisfying a particular angular resolution be selected and applied to the X-ray detector 28. If the monochromator 22 is constituted by an X-ray beam conditioning device of the same type as the device 1A of FIG. 3 or the device 1B of FIG. 6, according to this invention, the sample S can be irradiated with X-ray that has been completely monochromatised. If the analyzer 26 is constituted by an X-ray beam conditioning device of the same type as the device 1A of FIG. 3 or the device 1B of FIG. 6, according to this invention, X-ray satisfying a particular angular resolution can be selected from X-ray emitted from the sample S and can be applied to the X-ray detector 28. That is, very reliable data can be obtained if the X-ray beam conditioning device according to this invention is used as a monochromator or analyzer in an apparatus for measuring rocking curves.

Third Embodiment of the X-Ray Analysis Apparatus

Figure 9A:
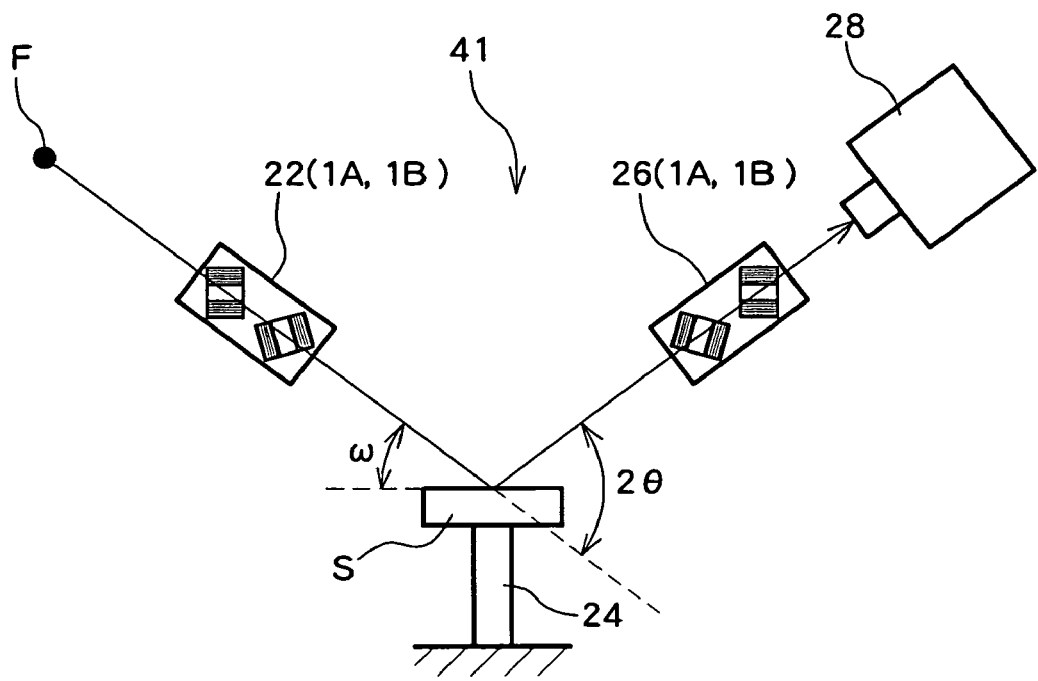
FIG. 9A is a front view showing still another embodiment of an X-ray analysis apparatus according to the present invention.

FIG. 9A shows still another embodiment of an X-ray analysis apparatus according to the present invention. In the embodiment the present invention is applied to a reciprocal space map measuring apparatus. It should be noted that FIG. 9A only outlines the X-ray analysis apparatus. Accordingly, FIG. 9A shows the essential components only, not illustrating the lesser components of this X-ray analysis apparatus.

The reciprocal space map measuring apparatus 41 has an X-ray source F, a monochromator 22, a sample holder 24, an analyzer 26, and an X-ray detector 28. The sample holder 24 supports a sample S to be analyzed, and holds the sample S at a prescribed position. The monochromator 22 and the analyzer 26 are each constituted by an X-ray beam conditioning device of the same type as the device 1A shown in FIG. 3 or the device 1B shown in FIG. 6.

Figure 9B:
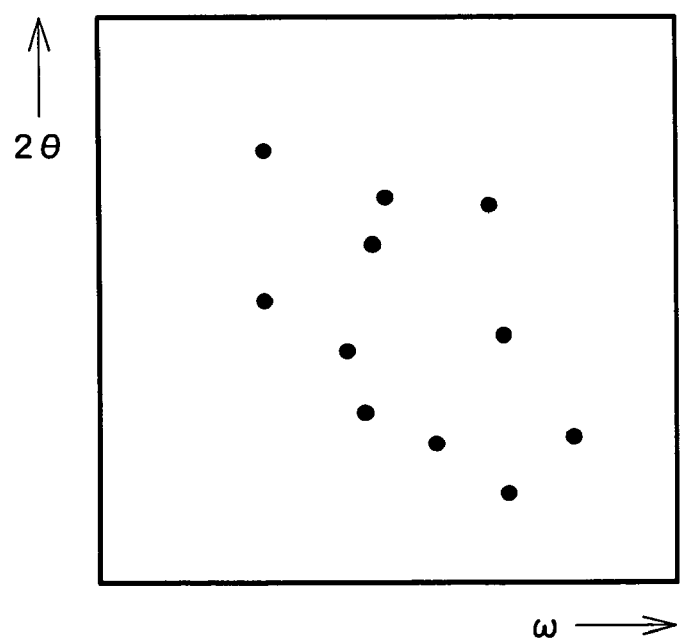
FIG. 9B is a diagram representing the results of measuring performed by using the apparatus shown in FIG. 9A.

In the reciprocal space map measuring apparatus 41, the X-ray detector 28 detects X-ray diffracted by the sample S, while it gradually changes and sets at angle 2θ to the incident X-ray and while it is scanning the incident angle ω of X-ray applied to the sample S. The results provided by the reciprocal space map measuring apparatus 41 are recorded as dot data that represents dots in a coordinates plane as is illustrated in FIG. 9B. In FIG. 9B, the incident angle ω of the X-ray is plotted on the axis of abscissas and the diffraction angle 2θ is plotted on the axis of ordinates. The density of each dot data shows the intensity of the diffracted X-ray generated at the sample S.

To enable the reciprocal space map measuring apparatus 41 to provide reliable data, it is desirable to irradiate the sample S with X-ray that has been completely monochromatised. For the same purpose, it is desired that only X-ray satisfying a particular angular resolution be selected and applied to the X-ray detector 28. If the monochromator 22 is constituted by an X-ray beam conditioning device of the same type as the device 1A of FIG. 3 or the device 1B of FIG. 6, according to this invention, the sample S can be irradiated with X-ray that has been completely monochromatised. If the analyzer 26 is constituted by an X-ray beam conditioning device of the same type as the device 1A of FIG. 3 or the device 1B of FIG. 6, according to this invention, X-ray satisfying a particular angular resolution can be selected from X-ray emitted from the sample S and can be applied to the X-ray detector 28. That is, very reliable data can be obtained if the X-ray beam conditioning device according to this invention is used as a monochromator or analyzer in an apparatus for measuring reciprocal-space maps.

Fourth Embodiment of the X-Ray Analysis Apparatus

Figure 10A:
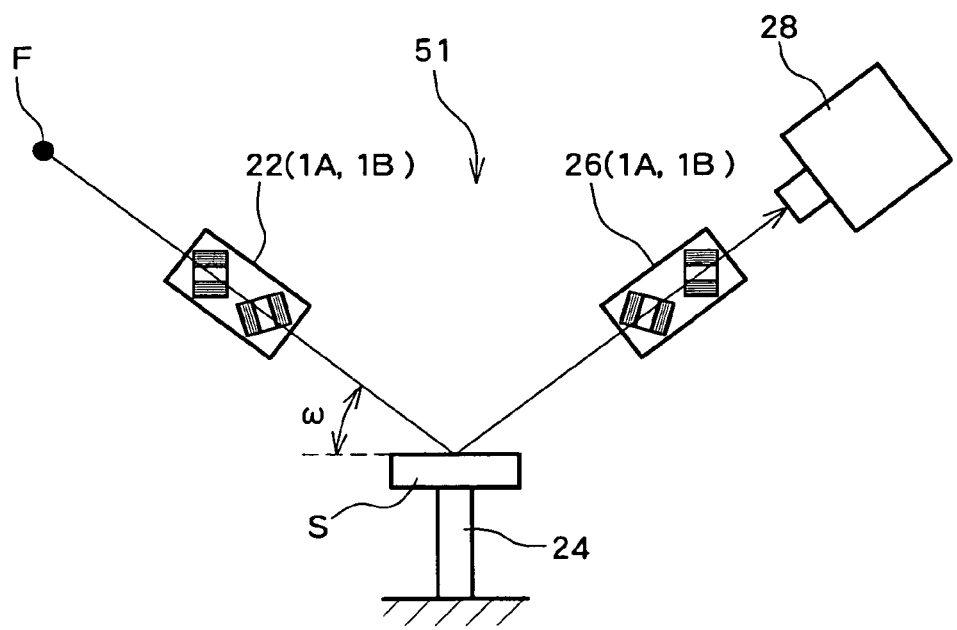
FIG. 10A is a front view showing still another embodiment of an X-ray analysis apparatus according to the present invention.

FIG. 10A depicts still another embodiment of an X-ray analysis apparatus according to this invention. In the embodiment the present invention is applied to a reflectivity measuring apparatus. Note that FIG. 10A only outlines the X-ray analysis apparatus. Accordingly, FIG. 10A shows the essential components only, not illustrating the lesser components of this X-ray analysis apparatus.

The reflectivity measuring apparatus 51 has an X-ray source F, a monochromator 22, a sample holder 24, an analyzer 26, and an X-ray detector 28. The sample holder 24 supports a sample S to be analyzed, and holds the sample S at a prescribed position. The monochromator 22 and the analyzer 26 are each constituted by an X-ray beam conditioning device of the same type as the device 1A shown in FIG. 3 or the device 1B shown in FIG. 6.

Figure 10B:
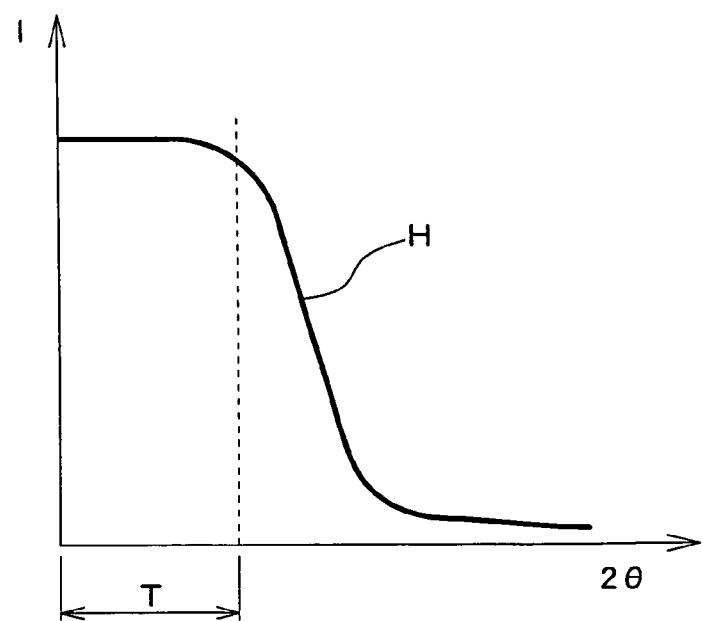
FIG. 10B is a diagram representing the results of measuring performed by using the apparatus shown in FIG. 10A.

The reflectivity measuring apparatus 51 operates as will be described below. X-ray is applied to the sample S at a small incident angle ω of, for example, about 0.1° to 4° to thereby totally reflect at the sample S. The X-ray detector 28 detects X-ray thus reflected, while scanning the sample S within a predetermined angle range around the sample S, and while the detecting angle 2θ of the X-ray detector 28 is kept at an angle twice as large as the incident angle ω. The scanning operation of the X-ray detector 28 is referred to as a 2θ/ω scan. In this manner, the structure of, for example, the thin surface region of the sample S is analyzed. The results provided by the reflectivity measuring apparatus 51 are recorded as data representing such a reflectivity curve H as shown in FIG. 10B. In FIG. 10B, the diffraction angle 2θ is plotted on the axis of abscissas and the X-ray intensity I is plotted on the axis of ordinates. As seen from FIG. 10B, the total reflection takes place in a region T where the angle 2θ is small and the intensity of the totally reflected X-ray abruptly decreases upon reaching a certain limit.

To enable the reflectivity measuring apparatus 51 to provide reliable data, it is desirable to obtain a reflectivity curve H that is sharp and not burred. To obtain a sharp reflectivity curve H, it is desirable to irradiate the sample S with X-ray that has been completely monochromatised. Also, it is desired that only X-ray satisfying a particular angular resolution be selected from the sample S and applied to the X-ray detector 28. If the monochromator 22 is constituted by an X-ray beam conditioning device of the same type as the device 1A of FIG. 3 or the device 1B of FIG. 6, according to this invention, the sample S can be irradiated with X-ray that has been completely monochromatised. If the analyzer 26 is constituted by an X-ray beam conditioning device of the same type as the device 1A of FIG. 3 or the device 1B of FIG. 6, according to this invention, X-ray satisfying a particular angular resolution can be selected from X-ray emitted from the sample S and can be applied to the X-ray detector 28. That is, very reliable data can be obtained if the X-ray beam conditioning device according to this invention is used as a monochromator or analyzer in an apparatus for measuring the reflectivity of samples.

Other Embodiments

The present invention has been explained, describing some preferred embodiments. Nevertheless, the invention is not limited to the embodiments. Various changes and modifications can be made within the scope defined by the claims that will be set forth below.

In the embodiment of FIG. 3 for example, the crystal holder 3 is depicted as a rectangular one. Nonetheless, the crystal holder 3 can be shaped and structured differently if necessary. To drive the crystal holder 3, the motor 4 is used in the embodiment of FIG. 3 and the rotary mechanism 11 of tangent bar type is used in the embodiment of FIG. 6. A drive mechanism of any other type may be used instead.

What is claimed is:
1. An X-ray beam conditioning device comprising:
a crystal holder for supporting both a first crystal block that diffracts X-ray by a specific diffraction angle and a second crystal block that diffracts X-ray by a specific diffraction angle, said first crystal block and said second crystal block being fixedly mounted on said crystal holder, respectively, so that said second crystal block is configured to diffract X-ray emerging from said first crystal block; and crystal-angle adjusting means for rotating said crystal holder around an axis extending at a right angle to a plane including an optical axis of X-ray, and fixedly supporting said crystal holder at the rotated position, wherein said crystal holder rigidly holds said first crystal block and said second crystal block at such an angle to each other that both crystal blocks diffract X-ray, and said first crystal block and said second crystal block are channel-cut crystals that each have two X-ray reflecting surfaces, which oppose each other, said first crystal block is positioned nearer an X-ray source than said second crystal block, said crystal-angle adjusting means rotates said crystal holder to change an angle at which X-ray generated by said X-ray source is applied to one X-ray reflecting surface of said first crystal block, and a rotation axis of said crystal holder extends in one X-ray reflecting surface of said first crystal block.

2. The X-ray beam conditioning device according to claim 1, wherein said crystal-angle adjusting means has a motor whose output shaft is controllable according to a rotation angle, and said crystal holder is coupled directly to said output shaft of said motor.

3. The X-ray beam conditioning device according to claim 1, wherein said crystal-angle adjusting means has a rotary mechanism of a tangent bar type, and said crystal holder is secured to an output shaft of said rotary mechanism of the tangent bar type, wherein said rotary mechanism of the tangent bar type has a rotary stage fixedly holding said crystal holder, a control rod extending outwards from said rotary stage, an eccentric cam abutting on the end of said control rod, and a motor for rotating said eccentric cam.

4. An X-ray analysis apparatus comprising:
an X-ray source that generates X-ray to be applied to a sample;
X-ray detecting means for detecting X-ray emitted from said sample; and
an X-ray beam conditioning device that is arranged between said X-ray source and said sample,
wherein the X-ray beam conditioning device is the X-ray beam conditioning device described in claim 1.

5. The X-ray analysis apparatus according to claim 4, wherein said X-ray detecting means detects X-ray diffracted by said sample, while said X-ray detecting means is held at a specific angle relative to X-ray applied from said X-ray source to said sample, and while an angle at which X-ray is applied to said sample is being changed over an angle range for measuring rocking curve.

6. The X-ray analysis apparatus according to claim 4, wherein said X-ray detecting means detects X-ray diffracted by said sample, while an angle at which the X-ray detecting means is held relative to X-ray applied from said X-ray source to said sample is being changed, and while an angle at which X-ray is applied to said sample is being scanned.

7. The X-ray analysis apparatus according to claim 4, wherein an angle at which X-ray is applied to said sample is set to a small angle, and said X-ray detecting means detects X-ray totally reflected by said sample.

8. An X-ray analysis apparatus comprising:
an X-ray source that generates X-ray to be applied to a sample;
X-ray detecting means for detecting X-ray emitted from said sample; and
an X-ray beam conditioning device that is arranged between said sample and said X-ray detecting means,
wherein said X-ray beam conditioning device is the X-ray beam conditioning device described in claim 1.

9. An X-ray beam conditioning device comprising:
a crystal holder for supporting both a first crystal block that diffracts X-ray by a specific diffraction angle and a second crystal block that diffracts X-ray by a specific diffraction angle, said first crystal block and said second crystal block being fixedly mounted on said crystal holder, respectively, so that said second crystal block is configured to diffract X-ray emerging from said first crystal block; and crystal-angle adjusting means for rotating said crystal holder around an axis extending at a right angle to a plane including an optical axis of X-ray, and fixedly supporting said crystal holder at the rotated position, wherein said crystal holder rigidly holds said first crystal block and said second crystal block at such an angle to each other that both crystal blocks diffract X-ray, and said first crystal block and said second crystal block are channel-cut crystals that each have two X-ray reflecting surfaces, which oppose each other, said first crystal block is positioned nearer an X-ray source than said second crystal block, said crystal-angle adjusting means rotates said crystal holder to change an angle at which X-ray generated by said X-ray source is applied to one X-ray reflecting surface of said first crystal block, and a rotation axis of said crystal holder extends through said first crystal block other than at X-ray reflecting surfaces of said first crystal block.

10. The X-ray beam conditioning device according to claim 9, wherein said crystal-angle adjusting means has a motor whose output shaft is controllable according to a rotation angle, and said crystal holder is coupled directly to said output shaft of said motor.

11. The X-ray beam conditioning device according to claim 9, wherein said crystal-angle adjusting means has a rotary mechanism of a tangent bar type, and said crystal holder is secured to an output shaft of said rotary mechanism of the tangent bar type, wherein said rotary mechanism of the tangent bar type has a rotary stage fixedly holding said crystal holder, a control rod extending outwards from said rotary stage, an eccentric cam abutting on the end of said control rod, and a motor for rotating said eccentric cam.

12. An X-ray analysis apparatus comprising:
an X-ray source that generates X-ray to be applied to a sample;
X-ray detecting means for detecting X-ray emitted from said sample; and
an X-ray beam conditioning device that is arranged between said X-ray source and said sample,
wherein the X-ray beam conditioning device is the X-ray beam conditioning device described in claim 9.

13. The X-ray analysis apparatus according to claim 12, wherein said X-ray detecting means detects X-ray diffracted by said sample, while said X-ray detecting means is held at a specific angle relative to X-ray applied from said X-ray source to said sample, and while an angle at which X-ray is applied to said sample is being changed over an angle range for measuring rocking curve.

14. The X-ray analysis apparatus according to claim 12, wherein said X-ray detecting means detects X-ray diffracted by said sample, while an angle at which the X-ray detecting means is held relative to X-ray applied from said X-ray source to said sample is being changed, and while an angle at which X-ray is applied to said sample is being scanned.

15. The X-ray analysis apparatus according to claim 12, wherein an angle at which X-ray is applied to said sample is set to a small angle, and said X-ray detecting means detects X-ray totally reflected by said sample.

16. An X-ray analysis apparatus comprising:
an X-ray source that generates X-ray to be applied to a sample;
X-ray detecting means for detecting X-ray emitted from said sample; and
an X-ray beam conditioning device that is arranged between said sample and said X-ray detecting means,
wherein said X-ray beam conditioning device is the X-ray beam conditioning device described in claim 9.

17. An X-ray beam conditioning device comprising:
a crystal holder for supporting both a first crystal block that diffracts X-ray by a specific diffraction angle and a second crystal block that diffracts X-ray by a specific diffraction angle, said first crystal block and said second crystal block being fixedly mounted on said crystal holder, respectively, so that said second crystal block is configured to diffract X-ray emerging from said first crystal block; and
crystal-angle adjusting means for rotating said crystal holder around an axis extending at a right angle to a plane including an optical axis of X-ray, and fixedly supporting said crystal holder at the rotated position,
wherein said crystal holder rigidly holds said first crystal block and said second crystal block at such an angle to each other that both crystal blocks diffract X-ray, and
said first crystal block and said second crystal block are channel-cut crystals that each have two X-ray reflecting surfaces, which oppose each other,
said first crystal block is positioned nearer an X-ray source than said second crystal block,
said crystal-angle adjusting means rotates said crystal holder to change an angle at which X-ray generated by said X-ray source is applied to one X-ray reflecting surface of said first crystal block, and
a rotation axis of said crystal holder extends outside said first crystal block and passes a point closer to said X-ray source than to said first crystal block.

18. The X-ray beam conditioning device according to claim 17, wherein said crystal-angle adjusting means has a motor whose output shaft is controllable according to a rotation angle, and said crystal holder is coupled directly to said output shaft of said motor.

19. The X-ray beam conditioning device according to claim 17, wherein said crystal-angle adjusting means has a rotary mechanism of a tangent bar type, and said crystal holder is secured to an output shaft of said rotary mechanism of the tangent bar type,
wherein said rotary mechanism of the tangent bar type has a rotary stage fixedly holding said crystal holder, a control rod extending outwards from said rotary stage, an eccentric cam abutting on the end of said control rod, and a motor for rotating said eccentric cam.

20. An X-ray analysis apparatus comprising:
an X-ray source that generates X-ray to be applied to a sample;
X-ray detecting means for detecting X-ray emitted from said sample; and
an X-ray beam conditioning device that is arranged between said X-ray source and said sample,
wherein the X-ray beam conditioning device is the X-ray beam conditioning device described in claim 17.

* * * * *